United States Patent [19]

Corbett

[11] 4,386,029
[45] May 31, 1983

[54] PROCESS FOR THE PREPARATION OF ANTIBIOTICS

[75] Inventor: David F. Corbett, Reigate, England

[73] Assignee: Beecham Group Limited, England

[21] Appl. No.: 200,428

[22] Filed: Oct. 24, 1980

Related U.S. Application Data

[63] Continuation-in-part of Ser. No. 177,272, Aug. 11, 1980.

[30] Foreign Application Priority Data

Oct. 29, 1979 [GB] United Kingdom ................. 7937456
Apr. 17, 1980 [GB] United Kingdom ............... 80012724

[51] Int. Cl.$^3$ ........................................... C07D 487/04
[52] U.S. Cl. .............................................. 260/245.2 T
[58] Field of Search ................................. 260/245.2 T

[56] References Cited

U.S. PATENT DOCUMENTS 4,262,010  4/1981  Christensen et al. ........ 260/245.2 T
4,269,772  5/1981  Melillo et al. ................. 260/245.2 T
4,273,709  6/1981  Christensen et al. ........ 260/245.2 T

FOREIGN PATENT DOCUMENTS 4648  10/1979  European Pat. Off. .
7973  2/1980  European Pat. Off. .
2751597  5/1978  Fed. Rep. of Germany .

OTHER PUBLICATIONS

Methoden Der Organischen Chemie, vol. IX, 103, 114, Georg ThiemeVerlag (1955).
Wagner et al.; Synthetic Organic Chemistry; pp. 787-788 (1953).

Primary Examiner—Mary C. Lee
Attorney, Agent, or Firm—Jacobs & Jacobs

[57] ABSTRACT

The present invention provides a process for the preparation of a compound of the formula (O):

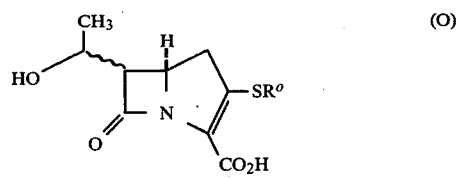

wherein $R°$ is $SCH_2CH_2NH_2$ which process comprises the reaction of a cleavable ester of a compound of the formula (O) wherein $R°$ is H with an optionally protected compound $XCH_2CH_2NH_2$ wherein X is a displaceable group.

10 Claims, No Drawings

PROCESS FOR THE PREPARATION OF ANTIBIOTICS

This is a continuation-in-part of Ser. No. 177,272, filed Aug. 11, 1980.

The present invention relates to a process for the preparation of β-lactam containing antibiotics and to the antibiotics when produced by that process.

The compounds of the formula (I):

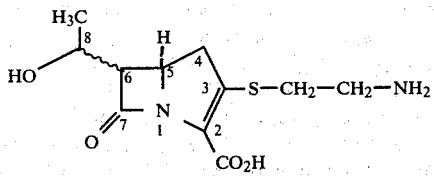

in which the hydroxyethyl moiety has the S-configuration at C-8 have been alleged to have been produced by the processes of Danish Patent Application Nos. 4880/77 and 4974/76. The first of these preparations of racemic compounds involved a considerable number of synthetic steps many of which did not appear to offer acceptable yields. Clearly it would be desirable to find a synthesis requiring fewer steps. The second of the aforementioned alleged preparations involved enzymatic cleavage of acetyl groups from natural products. Again this process did not appear to offer acceptable yields nor did it appear to produce an acceptably pure product. Clearly it would be desirable to provide a process for the preparation of the compounds of the formula (I) that involved few synthetic steps and produced a pure product. Such a process has now been found.

The present invention provides a process for the preparation of the compounds of the formula (I) as hereinbefore defined which process comprises the reaction of a cleavable ester of a compound of the formula (II):

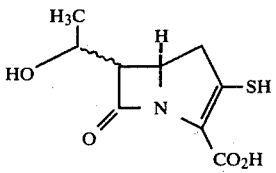

or thiolate of said ester, with a cleavable ester of a compound of the formula (III):

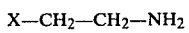

wherein X is a displaceable group, and thereafter cleaving the cleavable ester.

Suitable cleavable esters for use in this process include those cleavable by chemical methods such as hydrogenolysis or hydrolysis, or by biological methods, i.e. in-vivo hydrolysable esters. Particularly suitable are those cleavable by catalytic hydrogenation, for example the benzyl and substituted benzyl esters such as chlorobenzyl, methoxybenzyl and nitrobenzyl esters. A favoured cleavable ester for use in this invention is the p-nitrobenzyl ester. Examples of in-vivo hydrolysable esters include the acetoxymethyl, pivaloyloxymethyl, α-ethoxycarbonyloxymethyl and phthalidyl esters, of these the phthalidyl ester is preferred.

Generally the amino group in the compound of the formula (III) is protected in conventional manner during the course of the reaction, suitably as a —NH—$CO_2R$ moiety wherein R is a group such that $CO_2R$ is an ester, for example $CO_2R$ is a cleavable ester, wherein suitable cleavable esters are as described hereinabove.

Suitably X is a chlorine, bromine or iodine atom or a $CH_3SO_2O$ or $p\text{-}CH_3C_6H_4SO_2O$ group. A particularly apt value for X in the compound of the formula (III) is the bromine atom. As previously indicated a particularly suitable cleavable ester for use in the compound of the formula (III) is the p-nitrobenzyl ester. The reaction may be carried out on a thiolate salt of the ester of the compound of the formula (II) or more suitably the process may be carried out in the presence of an acid acceptor such as an alkali or alkaline earth metal carbonate or bicarbonate such as potassium carbonate. Suitably the reaction is carried out in polar organic solvents such as dimethylformamide. This step may also be carried out at a non-extreme temperature for example $-30°$ C. to $+30°$ C. and it is a considerable advantage of this process that an ambient temperature may be employed. The desired product may be obtained by diluting the reaction mixture after completion with water and a water immiscible solvent and thereafter evaporating the dried organic layer. If desired purification may be effected chromatographically, for example on silica eluting with ethyl acetate optionally containing small amounts of ethanol.

The cleavage of the ester groups by catalytic hydrogenation is generally carried out in a reaction medium maintained at approximate neutrality (that is pH 6–8, more suitably 6.5–7.5 and preferably at pH 7). This may be effected using a buffer such as a phosphate buffer in conjunction with a solvent system containing water and sufficient organic solvent to enable dissolution of the reactants, such as a mixture of water with dioxan optionally together with a lower alkanol such as ethanol. This step may also be carried out at a non-extreme temperature as hereinbefore defined and it is once more a considerable advantage that an ambient temperature can be used. A low ambient or elevated pressure of hydrogen may be employed but it has proved convenient to use an atmospheric pressure of hydrogen. The catalyst used will generally be a transition metal catalyst of which palladium has proved suitable. A preferred catalyst is palladium on carbon. After completion of the reaction the desired product may be obtained by filtering off the solids, diluting with water, washing the aqueous solution with an immiscible solvent such as ether or ethyl acetate and then removing the water, for example by evaporation under low pressure or by freeze drying. If desired a purification step may be employed, for example by chromatography using a resin such as XAD-2, XAD-4 or Diaion HP20.

A particular advantage of this process is that it yields a pure product that can be obtained in crystalline form. The esters of the compounds of the formula (II) may be prepared by the reaction of an ester of a compound of the formula (V) wherein the hydroxyethyl substituent has the S-configuration at C-8:

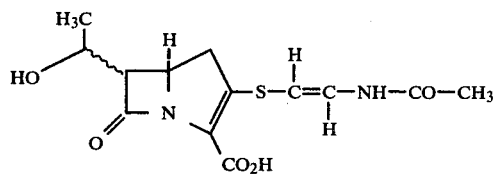

(V)

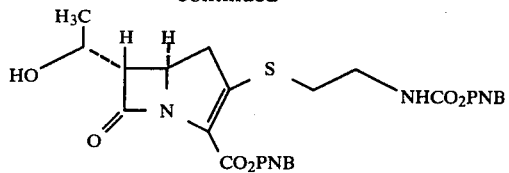

(e3)

with a source of hypohalous acid. Suitably the reaction is performed at a non-extreme temperature such as −30° C. to +30° C., preferably ambient. In general the solvent system used will be a homogeneous mixture of water and an inert organic solvent such as dioxan or acetone. Suitably the hypohalous acid is hypobromous acid or hypochlorous acid, of these hypobromous acid is preferred. Suitable sources of hypohalous acids include N-bromoacetamide, N-chloroacetamide and N-bromopropionamide.

The following Examples illustrate this invention. In the Examples PNB means p-nitrobenzyl and DMF means dimethylformamide.

EXAMPLE 1

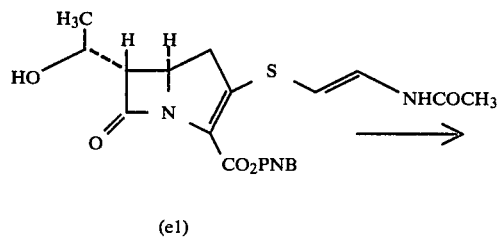

(e1)

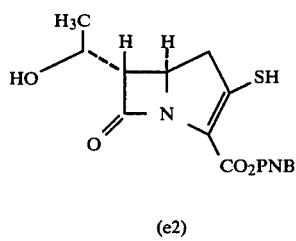

(e2)

(a) The ester (e1) (200 mg) was dissolved in a mixture of dioxan (4 ml) and water (0.5 ml) and to the solution was added with stirring a solution of N-bromoacetamide (62 mg) in dioxan (0.5 ml). After 5 mins at ambient temperature the solution was diluted with chloroform (30 ml) and then washed with water. The organic layer was dried (MgSO$_4$) and evaporated in vacuo to afford a foam containing (e2):

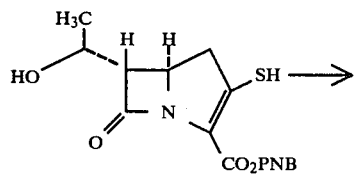

(e2)

(b) The foamy product (e2) was dissolved in DMF (3 ml) and to the solution was added anhydrous potassium carbonate (62 mg) and 2-p-nitrobenzyloxycarbonylaminoethyl bromide (135 mg). The mixture was stirred at room temperature for 20 min. before diluting with ethyl acetate (30 ml). The solution was washed with water (3×30 ml) and brine (20 ml), dried (MgSO$_4$) and concentrated in vacuo. The product was chromatographed on a column of silica gel using ethyl acetate as eluant.  p-Nitrobenzyl-(5R,6S)-3-(2-p-nitrobenzyloxycarbonylaminoethylthio)-6-[(s)-1-hydroxyethyl]-7-oxo-1-azabicyclo[3.2.0]hept-2-ene-2-carboxylate (e3) was obtained as a white solid (31 mg); ν$_{max}$ (KBr) 1775 and 1700 cm$^{-1}$; λ$_{max}$ (EtOH) 319 and 267 nm; δ [(CD$_3$)$_2$NCDO] 1.28 (3H, d, J 6 Hz, CH$_3$CH), ca. 3.0–3.6 (7H, m, 4-CH$_2$, SCH$_2$CH$_2$N and 6-CH), ca. 4.15 (2H, m, 5-CH and CH$_3$CH), 5.15 (1H, d, OH), 5.24 (2H, s, CO$_2$CH$_2$), 5.32 and 5.57 (each 1H, d, J 14 Hz, CO$_2$CH$_2$) ca. 7.6–7.9 (5H, m aromatic protons and NH) and 8.24 (4H, d, J 9 Hz, aromatic protons).

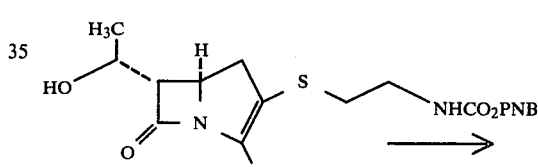

(e3)

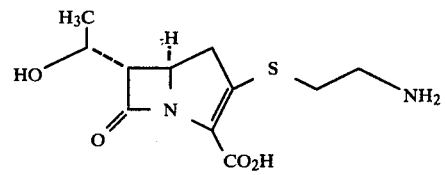

(e4)

(c) A mixture of the ester (e3) (30 mg), 10% palladium on charcoal (50 mg), dioxan (4 ml), water (1 ml), ethanol (0.3 ml) and 0.05 M pH 7 phosphate buffer solution (1.3 ml) was shaken under hydrogen for 2h. The catalyst was removed by filtration of the mixture over Celite washing with water (10 ml) and the solution was then concentrated to a volume of about 10 ml. The aqueous solution was washed with ether (3×20 ml) and ethyl acetate (10 ml) before concentrating in vacuo to a volume of about 3 ml. The solution was loaded onto a column (80×12 mm) of XAD-2, which was then eluted with water to afford (5R, 6S)-3-(2-aminoethylthio)-6-[(s)-1-hydroxyethyl]-7-oxo-1-azabicyclo[3.2.0]hept-2-ene-2-carboxylic acid (e4) which was identified by the absorption at λ$_{max}$ (H$_2$O) 297 nm in the uv spectrum.

EXAMPLE 2

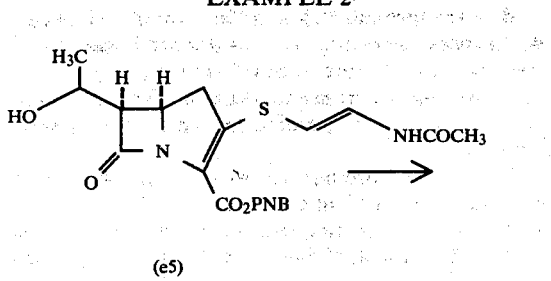

(e5)

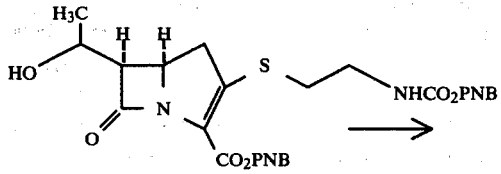

(e7)

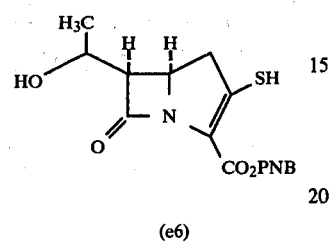

(e6)

CH$_3$C$\underline{H}$), 5.08 (1H, d, J 5 Hz, OH), 5.27 (2H, s, CO$_2$CH$_2$); 5.35 and 5.58 (each 1H, d, J 14 Hz, CO$_2$CH$_2$) ca. 7.6–7.9 (5H, m, aromatic protons and NH) and 8.28 (4H, d, J 9 Hz, aromatic protons).

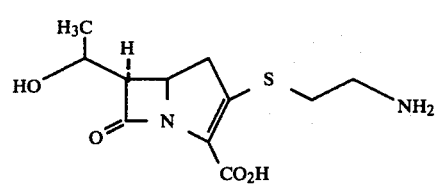

(e8)

(a) A solution of the ester (E5) (500 mg) in a mixture of dioxan (10 ml) and water (1.5 ml) was treated with a solution of N-bromoacetamide (154 mg) in dioxan (1 ml) for 5 min with stirring at room temperature. Chloroform (70 ml) was added and the solution then washed with water (50 ml), dried (MgSO$_4$) and concentrated in vacuo to yield (e6):

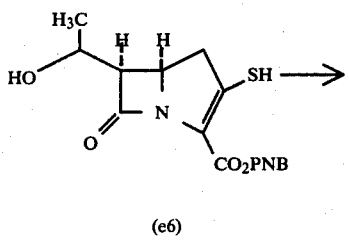

(e6)

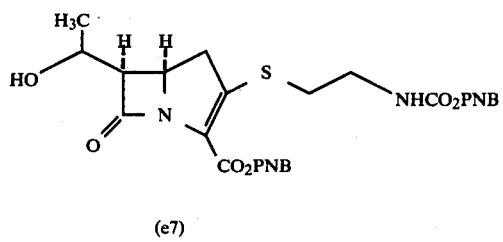

(e7)

(b) The residue (e6) was dissolved in DMF (7 ml) and the solution was stirred with anhydrous potassium carbonate (154 mg) and 2-p-nitrobenzyloxycarbonylaminoethyl bromide (339 mg) for 25 min. Ethyl acetate (70 ml) was added and the solution washed with water (3×50 ml) and brine (50 ml). Evaporation of the dried (MgSO$_4$) organic layer gave a product mixture which was chromatographed on silica gel using ethyl acetate followed by 5% ethanol in ethyl acetate to elute. Evaporation of solvent from the fractions containing the desired product (t.l.c) afforded p-nitrobenzyl (5R,6R)-3-(2-p-nitrobenzyloxycarbonylaminoethylthio)-6-[(s)-1-hydroxyethyl]-7-oxo-1-azabicyclo[3.2.0]hept-2-ene-2-carboxylate (e7) as a white solid (177 mg); $\nu_{max}$ (KBr) 1775 and 1740–1700 (br) cm$^{-1}$; $\lambda_{max}$ (EtOH) 315 ($\epsilon$11,830) and 264 ($\epsilon$18740) nm; δ [(CD$_3$)$_2$NCDO]1.31 (3H, d, J 6.5 Hz, C$\underline{H}_3$CH), ca. 3.05–3.75 (7H, m, 4-CH$_2$, SCH$_2$CH$_2$N and 6-CH), 3.95–4.45 (2H, m, 5-CH and (c) A solution of the ester (e7) (135 mg) in a mixture of dioxan (15 ml), water (4.5 ml), ethanol (1.35 ml) and 0.05M pH 7 phosphate buffer (6 ml) was hydrogenated over 10% palladium on charcoal (200 mg) for 2h. The mixture was filtered over Celite, washing with water (20 ml) and the filtrate was then concentrated in vacuo to a volume of about 25 ml. The aqueous solution was washed with ether (2×20 ml) and ethyl acetate (2×10 ml) and then concentrated to a volume of about 10 ml, before loading onto a column (20×2.5 cm) of XAD-2. Elution with water gave fractions containing (5R,6R)-3-(2-aminoethylthio)-6-[(s)-1-hydroxyethyl]-7-oxo-1-azabicyclo[3.2.0]hept-2-ene-2-carboxylic acid (e8) as characterised by the u.v. chromophore at $\lambda_{max}$ (H$_2$O) 296 nm. Some of the fractions were combined and freeze-dried to give the product as a solid.

What is claimed is:

1. A process for the preparation of a compound of the formula (I):

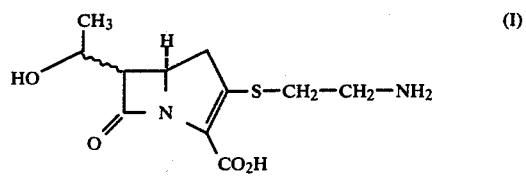

(I)

in which the hydroxyethyl moiety has the S-configuration at C-8, which process comprises the reaction of a chemically or biologically cleavable ester of a compound of the formula (II):

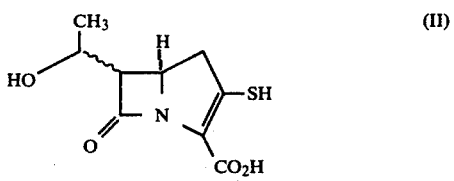

(II)

or thiolate of said ester, with a chemically or biologically cleavable ester of a compound of the formula (III):

$$X-CH_2-CH_2-NH_2 \quad (III)$$

wherein X is chlorine, bromine, iodine, CH$_3$SO$_2$O or p-CH$_3$C$_6$H$_4$SO$_2$O, and thereafter cleaving the cleavable ester by chemical or biological means.

2. A process according to claim 1 wherein the cleavable esters are those cleavable by catalytic hydrogenation.

3. A process according to claim 2 wherein the ester groups is benzyl, chlorobenzyl, methoxybenzyl or nitrobenzyl.

4. A process according to claim 1 wherein X is a bromine atom.

5. A process according to claim 1 wherein the compound of the formula (II) is in the form of a thiolate.

6. A process according to claim 1 wherein the process is carried out in the presence of an acid acceptor.

7. A process according to claim 6 wherein the acid acceptor is an alkali or alkaline earth metal carbonate or bicarbonate.

8. A process according to claim 1 wherein the process is carried out at ambient temperature.

9. A process according to claim 1 wherein the compound of the formula (III) is in the form of the p-nitrobenzyl ester.

10. A process according to claim 1 wherein the process is carried out in a polar organic solvent.

* * * * *